United States Patent [19]

Apple

[11] 4,210,136
[45] Jul. 1, 1980

[54] APPARATUS FOR AUTOMATIC VENTILATION OF THE LUNGS

[76] Inventor: Wayne R. Apple, P.O. Box 3370, Boulder, Colo. 80303

[21] Appl. No.: 945,644

[22] Filed: Sep. 25, 1978

Related U.S. Application Data

[62] Division of Ser. No. 815,659, Jul. 14, 1977, Pat. No. 4,141,355.

[51] Int. Cl.² .................. A62B 7/00; A61M 15/00
[52] U.S. Cl. .................... 128/204.21; 128/205.18; 92/13.1
[58] Field of Search ............. 128/145.6, 145.5, 145.7, 128/145.8, 185; 74/575, 595, 600

[56] References Cited

U.S. PATENT DOCUMENTS

| | | | |
|---|---|---|---|
| 3,149,591 | 9/1964 | Aiki et al. | 74/575 |
| 4,076,021 | 2/1978 | Thompson | 128/145.6 |

Primary Examiner—Robert W. Michell
Assistant Examiner—Thomas J. Wallen
Attorney, Agent, or Firm—Richard D. Law

[57] ABSTRACT

A piston type air pump, for forced lung ventilation, with a variable length of stroke and a variable timing of inspiratory and expiratory phases. The pump includes a stepless change, variable radius crank arm, controllable during pump operation for changing the volume capacity of the pump. The drive motor is arranged for movement for varying the timing of piston in-movement to the piston out-movement for varying the time ratio of inspiration to expiration.

4 Claims, 22 Drawing Figures

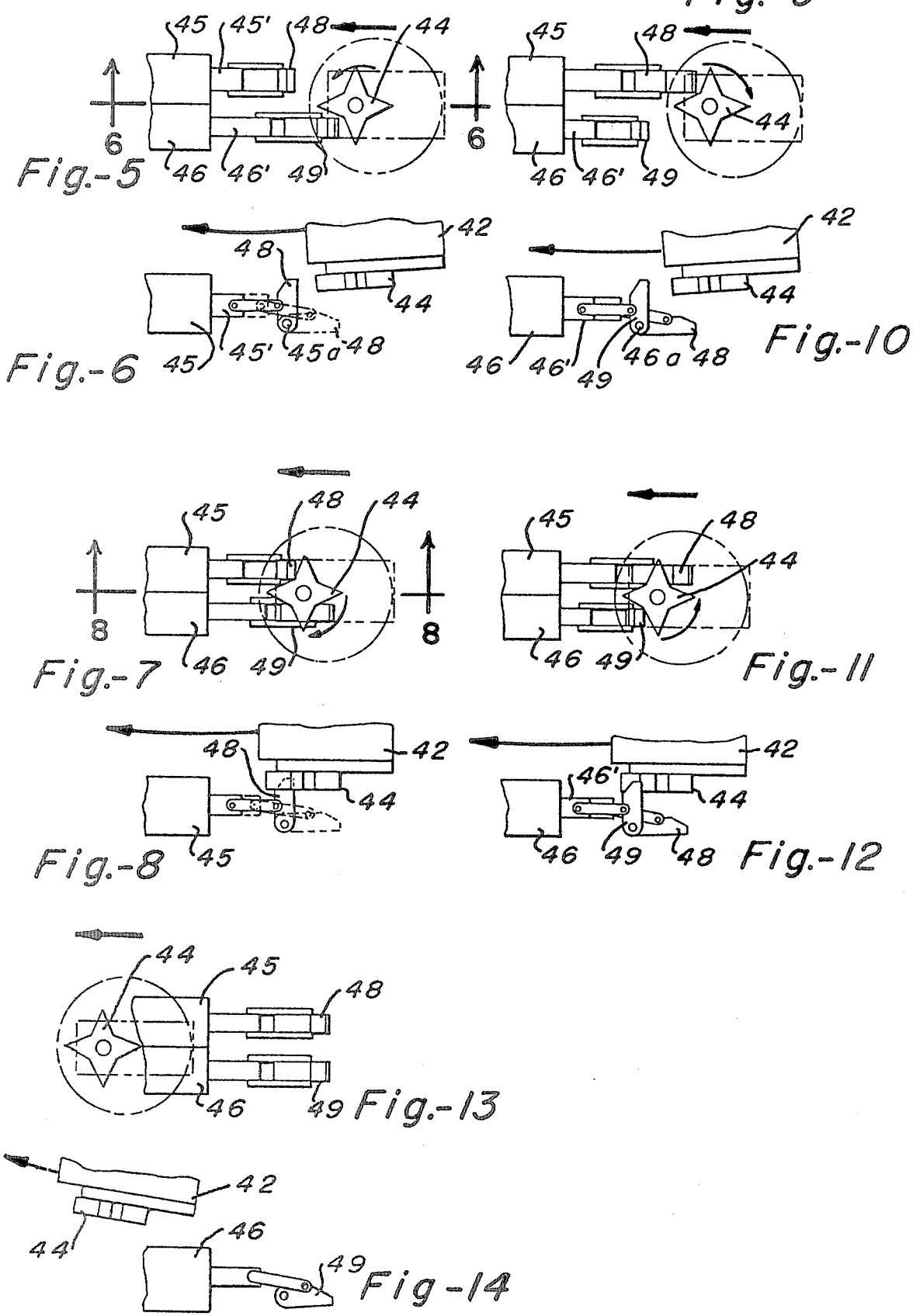

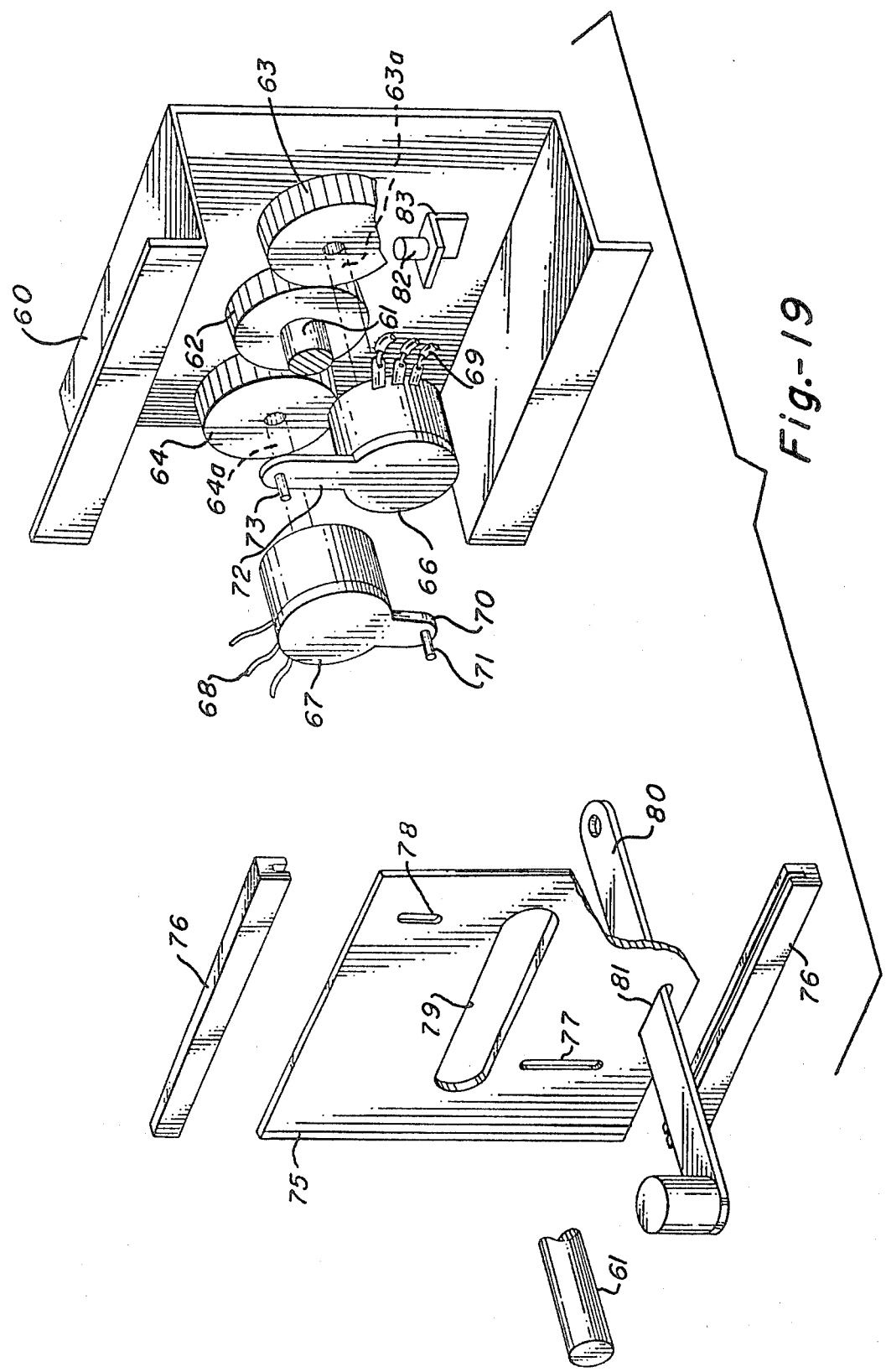

4,210,136

APPARATUS FOR AUTOMATIC VENTILATION OF THE LUNGS

This is a division of application Ser. No. 815,659, filed July 14, 1977, now U.S. Pat. No. 4,141,355.

PRIOR ART

In medical treatment of patients, controlled respiration is increasing being used for ventilating lungs in all types of respiratory insufficiencies. For some patients, controlled respiration is a way to life. Hospitals generally have large respiratory machines and the personnel to adequately control them. However, some ambulatory and out patients require ventilation and smaller, mobile respiratory machines are needed. A number of different types of ventilating equipment exists. Ventilators of the portable variety are generally electric motor driven, and the air movers include diaphragm pumps, squeeze bags, bellows, piston pumps, etc. as the motivative power for the air flow.

Normal respiration occurs at a rate of about 16 breaths per minute. The time for inhalation of air is normally 40% of each breath, with exhalation about 60% (referred to as I/E ratio). In a piston type pump, using a constant speed motor, the inhalation and exhalation take 50% of the breath. While this is adequate for some patients, it is highly desirable to change the inhalation to exhalation (I/E) ratio in many cases. Also, it is necessary to vary the volume of the air pumped, which requires different piston displacement to provide a different volume of air.

A complicated eccentric mechanical linkage may be used to change the I/E ratio in piston pumps, but with each specific eccentric, the ratio is constant, Thus, a change of eccentric is usually necessary to change the ratio. Prior art devices, also, have provided a changable volume of air pumped with each stroke, but the motor had to be stopped to change the effective radius of the crank arm to vary the piston displacement.

THE PRESENT INVENTION

According to the present invention, there is provided a portable ventilator having a variable, effective crank arm radius for operation of the pump to either increase or decrease the volume of air pumped. A variable speed motor is controlled by two potentiometers to control the timing of the I/E ratio, changing the timing of in-movement to out-movement of the piston. Means are provided to exercise such control during motor operation. A piston is provided with a thin face portion with guide brackets so that the motor nests closely to the cylinder reducing over all length of the unit at maximum stroke.

OBJECTS OF THE INVENTION

Included among the objects and advantages of the invention is to provide an efficient, easily controlled portable ventilator.

Another object is to provide a ventilator with an improved construction and assembly of a piston air pump, drive motor and a variable crank arm varying piston displacement during operation.

Still another object of the invention is to provide control means for a drive motor for a piston pump to varying the ratio of the timing of each half of each piston cycle during operation of the motor.

Yet another object of the invention is to provide respiratory alarms for inadequate or excess pressure and/or failure of the equipment.

An additional object of the invention is to provide circuits for three power sources for a portable ventilator.

A still additional object of the invention is to provide a portable respirator or ventilator which has easily accessible controls for varying the operating parameters of the unit during operation.

These and other objects and advantages of the invention may be readily accertained by reference to the following description and appended illustrations.

GENERAL DESCRIPTION OF DRAWINGS

FIG. 5 is a top plan view of a control for varying the length of the connecting rod for the piston.

FIGS. 6–14 are top and side views of the control mechanism of FIG. 5 in various stages of operation to show the changing means for varying piston displacement.

FIG. 19 is an exploded perspective view of the mechanism for controlling a pair of potentiometers for varying motor speed for each half of a cylcle of a piston.

Figure 1:
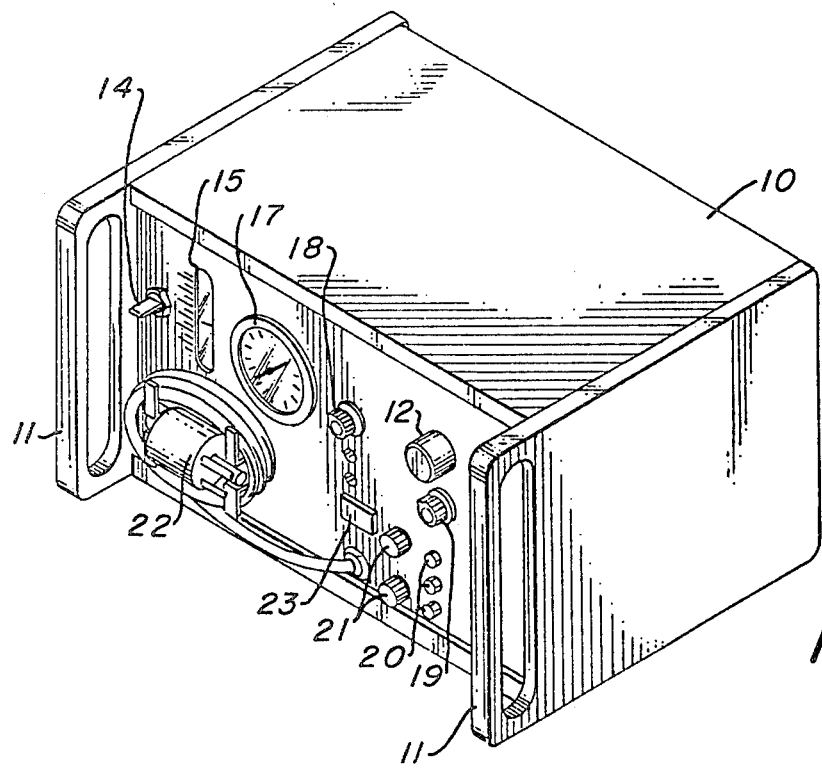
FIG. 1 is a perspective view of a ventilator, according to the invention, illustrating its mounting in a housing with the controls accessible to a user.
Figure 3:
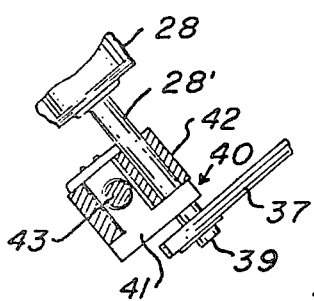
FIG. 3 is an enlaraged detail of an adjustable crank arm attachment to a motor.
Figure 2:
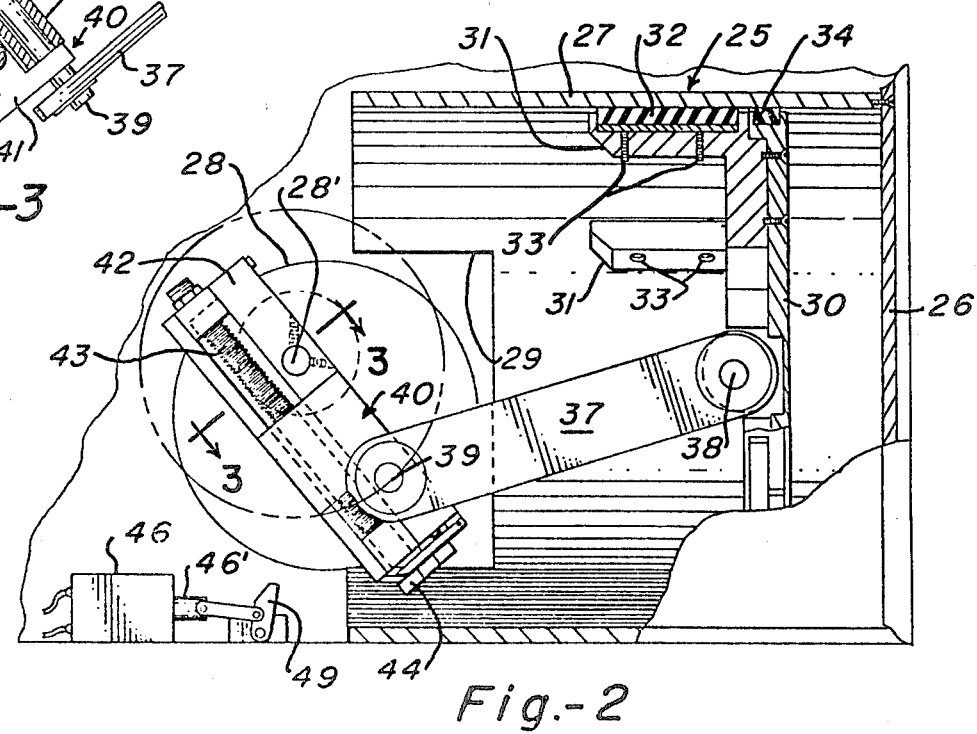
FIG. 2 is a side elevational view, in broken away detail, of a motor and air pump according to the invention.
Figure 4:
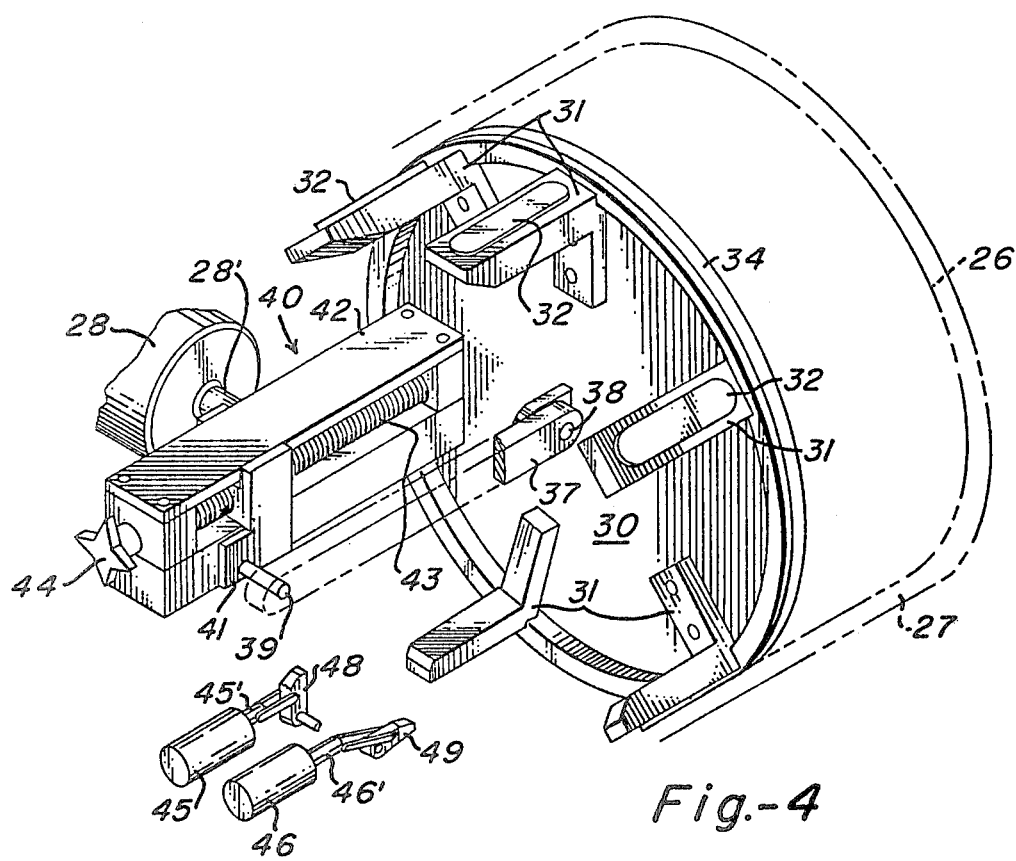
FIG. 4 is an enlarged detail, in broken away perspective, of a piston pump according to the invention.

A portable unit is shown in FIG. 1, which includes a housing 10 provided with manipulating handles 11 for ease in handling the unit. The housing for one mobile unit is approximately 8¾ inches × 10¼ inches × 12 inches, which permits the unit to be used with wheel chairs, and other ambulatory devices for patients. On the front panel of the unit between the handles 11 are the major operating controls. These include an air outlet 12 into which the patients air tube is inserted. A spring loaded volume control toggle switch 14 provides means for changing the volume of air, with a guage 15 to indicate the volume of the air output for each piston stroke. The mechanism for changing the volume is explained below. The pressure of the air for ventilation is shown in a pressure guage 17, and it is controlled by a rotary switch 18. The rate of ventilation, in breaths per minute, is controlled by a switch 19, which may be provided with an indicator dial to indicate the actual number of breaths. The power source for the unit may be a three source system including 110 VAC, 12 VDC and an internal battery. Lights 20 provide means for showing which circuit is being used for powering unit. Fuses 21 provide means for controlling over voltage. The unit may be hooked up to exterior battery by means of an outlet 23 which is connected to a cable from the battery, An electric power line 22 provides means for connection for the unit to 110 VAC. Circuitry for the sources and powering various units is conventional.

The air motivation unit is a piston pump driven by an electric motor, with a variable radius crank arm, explained below. The variable radius crank arm may be adjusted while the motor is running. The volume of air pumped may be adjusted, for example from 0 to 3,000 cc, and the rate adjusted from 8 to 30 breaths per minute. The cylinder and piston are arranged for close coupling to the drive motor which permits the large piston, approximately 7 inches in diameter, to travel a maximum stroke to provide about 3,000 cc of air maintaining a short overall length. The cylinder, shown in general by numeral 25, includes a head 26 and a cylinder wall 27 which extends axially of the head 26. A cut-out 29 is provided from the open end into the cylinder wall 27, to permit placement of a drive motor 28 close to the cylinder head 26. The distance cut into the wall 27 permits maximum travel of a piston mounted in the cylinder. Piston 30 is reciprocably mounted in the cylinder 25, and it is provided with five angle brackets 31 extending rearwardly from the piston head 30. Each bracket is provided with a bearing block 32 for riding on the cylinder wall. The bearing blocks are made of low friction plastic and are arranged to be positioned firmly against the cylinder wall by means of adjusting screws 33 to compensate for any irregularities in the cylinder dimensions. The brackets guide the piston in the cylinder and prevent the piston head 30 from wabbling in the cylinder. A seal ring 34 mounted around the periphery of the piston head 30 provides a seal for the piston on the cylinder wall. The seal ring may be a low friction plastic for sealing the piston and completing the pumping chamber. A connecting rod 37 is connected by a wrist pin 38 to the piston head 30 at one end and to a pin 39 on a volume adjustment assembly 40 which is attached to the motor 28. This volume adjustment mechanism 40 is in effect variable radius crank arm which transfers the motor rotation to the piston by means of the connecting rod.

The cutout 29 is formed in the cylinder wall, to provide means of positioning the motor, as explained above. The brackets 31, however, are arranged to ride in the cylinder wall remaining from the cut-outs. Thus, three brackets are mounted on the top, and two are mounted on the bottom. The five brackets provide adequate support for the piston head. In one form, the three upper brackets are spaced in about a 100° arc and the lower brackets are placed on a 30° arc, all riding on the cylinder wall.

The variable adjustment for piston stroke includes a sliding block 41 arranged to move reciprocably of a housing 42. The housing is pinned to motor shaft 28' at one side and longitudinally off-center of the housing 42. A jack screw 43 mounted in the housing 42 threadedly engages the block 41 and provides reciprocation of the block in relation to the housing 42. The pin 39 is mounted on the block 41 and it moves radially in relation to the motor shaft 28' thereby resulting in a variable radius crank arm which when connected to the piston by the connecting rod results in a variable piston stroke and variable pumping volume. The jact screw 43 is rotated by means of a star handle or ratchet wheel 44 when engaged by one of the actuator or pawls connected to a pair of solenoids 45 and 46. A pawl 48, connected to the plunger of solenoid 45 or a pawl 49 attached to the plunger 46' of the solenoid 46', provides means for turning the ratchet 44 clockwise or counter clockwise. The solenoids are positioned so that the ratchet wheel 44 may be turned one way or another by the activator on the end of the solenoid plunger. The solenoids are activated one at a time so as to permit an activator to engage the ratchet wheel. When the block 42 rotates, and one of the activators contacts the ratchet wheels it will rotate the threaded shaft or jack screw ¼ of a revolution, which moves block 41 and pin 39 changing the distance from the motor shaft to the pin resulting in a change of the radius of the crank arm. Depending on whether the ratchet wheel is moved clockwise or counter clockwise, the effective radius is increased or decreased. One revolution will result in a movement of the block to produce a 20cc change in volume of output, whether increased or decreased. The toggle switch 14 is connected to the solenoids 45 and 46, and movement in one direction activates one solenoid and in the other direction it activates the other solenoid to increase or decrease the volume. The toggle switch normally off and spring loaded to return to off when the switch lever is released. The volume indicator 15 may be a simple slide indicator on the scale with the slide connected by levers to the piston to show the volume output of the piston.

As shown in FIGS. 5–12 the turning of the ratchet wheel 44 is accomplished by means of the solenoids and activators. In FIGS. 5–8 solenoid 46 is inactive while solenoid 45 is activated. With the solenoids inactivated the activators are in a down position. On activating the solenoid 45, the activator which is pivoted on a pivot pin 45a is raised by the retraction of the plunger 45' into the solenoid. On rotation of the block 42, the ratchet wheel 44 engages the activator 48 as shown in FIG. 7 and 8 to rotate the ratchet wheel 45 a quarter of a turn as the block passes the activator. The ratchet wheel 44 is rotated in the opposite position by inactivating solenoid 45 and activating 46 to raise the activator 49 in position to be contacted by the wheel as the block 42 is rotated. Thus, in FIGS. 9–12 when the solenoid 46 is activated it withdraws the plunger 46 to raise the activator 49 to be contacted by one of the points of the passing ratchet wheel 44. Movement of the block 42 in its rotation moves the ratchet wheel 44 to contact the upstanding activator 49 and rotate the ratchet wheel 44 in a counter-clockwise motion, turning the jack screw one quarter of a revolution. With both of the solenoids 45 and 46 deactivated the plungers, normally spring loaded, withdraw from the solenoid and force the activators into a down, inactivated position, as shown in FIGS. 13 and 14. Thus, the rotation of the block 42 does not cause a contact of the ratchet wheel 44 with any of the activators, and, therefore, the pump remains at a constant pumping volume.

Figure 15:
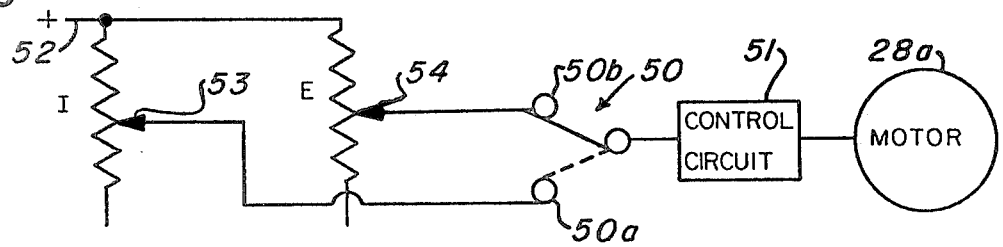
FIG. 15 is a schematic wiring diagram for a two potentiometer operating circuit of an electric motor.

As explained above, normal human respiration occurs at a rate of about 16 breaths per minute. Inhalation time is normally about 40% of each breath and the exhalation time is 60% . A variable speed motor is normally used to drive air pumps of the type in question, but the piston operates on each revolution. Normally the piston produces 50% inhalation as well as 50% exhalation. By using two potentiometers to drive the motor the ratio of inhalation to exhalation (I/E) may be changed. A simple wiring diagram is shown in FIG. 15, wherein a potentiometer I and a potentiometer E, through a swithcing circuit, shown in general by numeral 50, provides power to control circuit 51 for an electric motor 28a.

Figure 16:
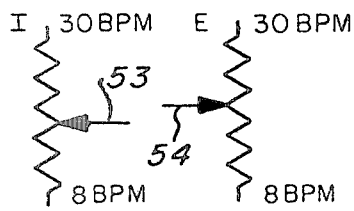
FIGS. 16–18 are schematic views for detailing the operation of the two potentiometers of FIG. 15 for changing the I/E ratio.
Figure 17:
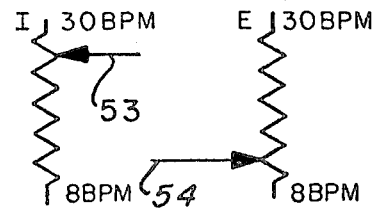
Figure 18:
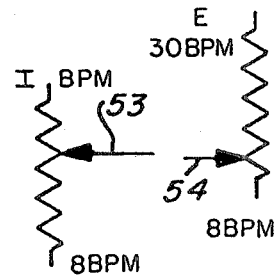

The control circuit 51 is a simple standard control circuit for operating the motor 28a. The switching means 50 is mechanically actuated by each half cycle of the motor. A current supply line 52 provides the positive side of the electric supply to each end of the potentiometers E and I, while the opposite side is connected to ground. Variable pickoff 53 of the potentiometer I is connected to one side 50A of the switch, while the pick-off 54 is connected to the other side of the switch 50b. As shown in FIG. 16, the potentiometers are balanced, with each potentiometer arranged to provide a motor speed from 8 to 30 rpm. By controlling the voltage of approximately half of each potentiometer pickoff the system provides a motor speed of 18 rpm. Thus, while each potentiometer is set for 18 rpm it controls only half of the motor cycle so that the total motor output is 18 cycles per minute. This gives an I/E ratio 1:1, resulting in a 50% inhalation and a 50% exhalation. When higher or lower rates are required, both potentiometers may be moved so that the pickoffs are still balanced, giving an I/E ratio of 1:1 regardless of the number of breaths per minute. For such purposes the potentiometers may be coupled and driven from a single shaft. If a new I/E ratio is desired, for example 1:1.5, the inhale rate would have to be increased to $22\frac{1}{2}$ breaths per minute while the exhale rate would have to be decreased to 15 breaths per minute. The potentiometer pickoffs would be moved out of balance as shown in FIG. 17 and could not be connected by a common shaft. To eliminate this offset and make possible the use of a single shaft the potentiometer bodies rather than the pickoff could be moved as shown in FIG. 18 resulting in a new I/E ratio without separate rate shafts. The mechanism for providing the variable I/E ratio is shown in FIG. 19, wherein a housing 60 provides support for the mechanism. A shaft 61 extends through the housing and is rotably supported thereby. The knob is on the other side and not shown. A gear 62 meshes with gears 63 and 64 on each side so that rotation of the shaft 61 turns the gear 62, which in turn turns the gears 63 and 64. Gear 64 is mounted on a shaft 64a and potentiometer 67 is mounted on the shaft and is rotated thereby. The potentiometer 67 is connected to the inhalation side of the motor control, and, therefore, is designated as the I potentiometer. An exhalation potentiometer 66 is mounted on a shaft 63a and the potentiometer 66 rotates conjointly with the gear 63; it is designated E. Each potentiometer is arranged with leads to the motor control circuit, thus potentiometer 67 has leads 68 while the potentiometer 66 has leads 69 both of which go to the motor control circuit. Potentiometer 67 has an ear or arm 70 and a pin 71, while the potentiometer 66 has an ear or arm 72 and a pin 73. A slideplate 75, mounted in to slide in slot bars 76 at the top and bottom and which are connected to the housing 60, provides means for changing the rate I/E. When assembled pin 71 extends through a slot 77 in the plate while pin 73 extends through a slot 78. Shaft 61 extends through horizontal slot 79 whereby the slideplate 75 can be moved back and forth without moving the shaft 61. A control lever 80, extending through a slot 81 in the plate, is mounted on a pivot pin 82 (which in turn is mounted on the bracket 83 secured to the housing 60). The lever 81 is pivotally mounted on the pin 82 and by lateral movement of the lever arm, the slideplate 85 moves laterally in the slot or groove bars 76. As the bar 80 is moved back and forth, the slideplate moves back and forth which in turn rotates the pins 71 and 73 to rotate the potentiometers. The rotation of the potentiometers results in the offset required of the pickoff of the potentiometers to obtain a desired I/E ratio. The ear 70 holding pin 71 is shorter than the ear 72 holding pin 73 to offset the difference in the control circuit.

The rate of breaths per minute is controlled by turning the shaft 61, which in turn rotates the potentiometers equally so that the pickoffs remain in their respective positions to produce the I/E constant ratio, but at variable breath rates. The ratio may be changed by movement of the bar 80 which rotates the potentiometers in relation to their pickoffs.

Figure 21:
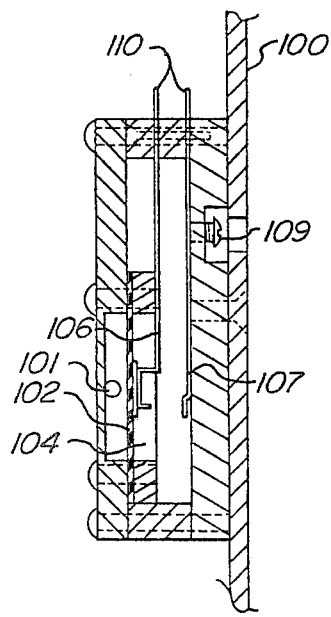
FIG. 21 is a side elevation of a pressure sensor according to the invention.
Figure 22:
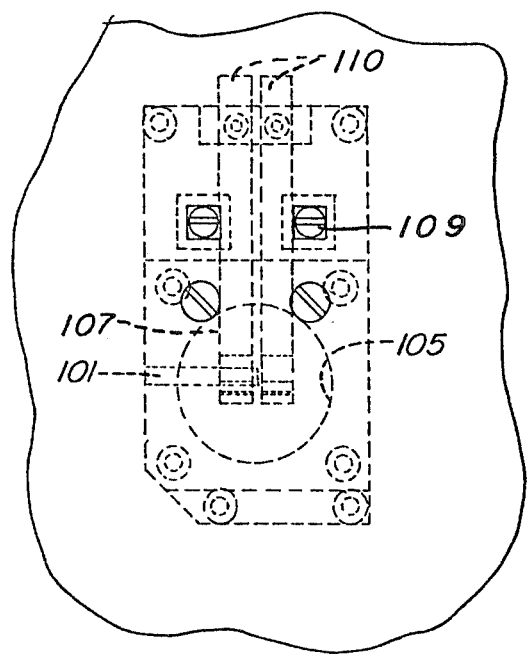
FIG. 22 is a front elevation of the device of FIG. 19.
Figure 20:
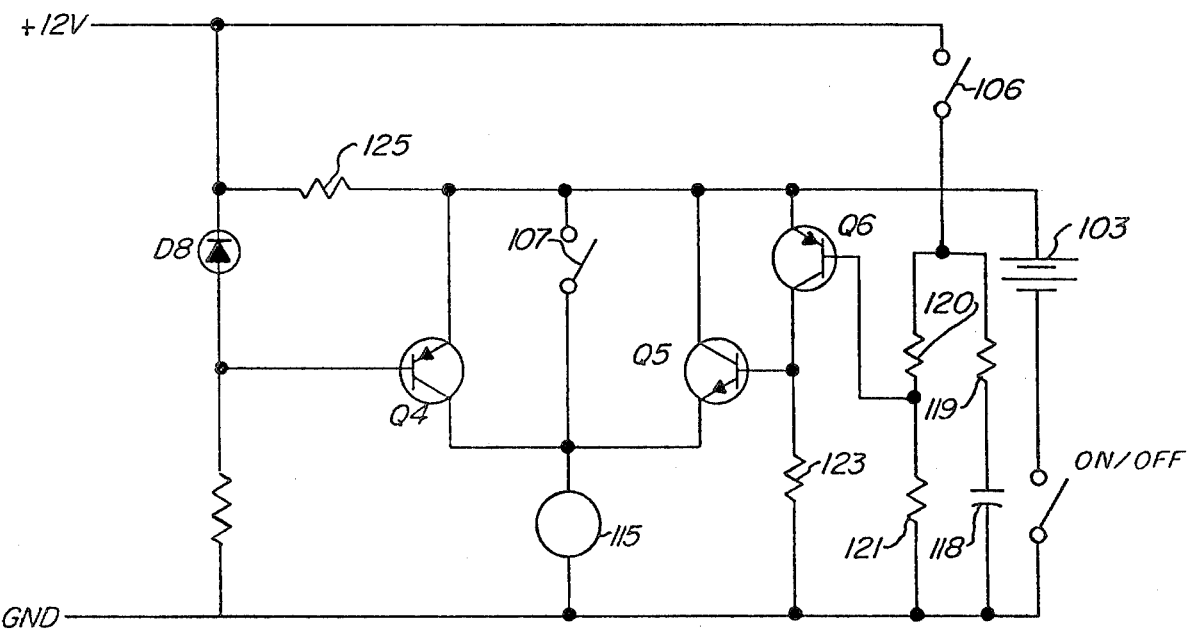
FIG. 20 is a schematic wiring diagram for an alarm circuit for a ventilator according to the invention.

Respiratory alarms are necessary on ventilators to assure proper performance and provide patient safety. A safety device is illustrated in the drawings FIGS. 21-22. It is mounted on a plate 100 and air pressure is provided through inlet 101 to a rubber diaphragm 102. The diaphragm is retained by plate 104 with a central hole 105 which permits the diaphragm to expand. The diaphragm, under air pressure, expands against a set of electric contacts 106. An adjusting screw 109 provides controls for the contacts. Electric leads 110 connected to the contacts provide a circuit to the alarm circuit. The switch 107 is activated when the predetermined pressure is exceeded, connecting a 3.6 v battery 103 to sound an alarm 115, FIG. 20. As soon as the pressure decreases below the predetermined level, the alarm stops. The alarm is an audible signal easily discernable by the user.

A low pressure alarm requires a delay circuit, since it would sound between each breath of normal breathing when the pressure drops to zero. The low pressure switch 106 closes each time the pressure increases above the preset minimum pressure level. This closure charges capacitor 118 (50 mfd) through a 220 ohm resistor 119, which begins to discharge through 1K resistor 120 and 120K resistor 121. If the low pressure switch does not close again within about 10 seconds, the capacitor discharges sufficiently to drop the base voltage on the transistor Q6 so it turns on which increases the voltage across 27K resistor 123. This voltage turns in the transister Q5 which sounds the alarm 115. As soon as the capacitor 118 is recharged the alarm shuts off. This alarm circuit, also, provides a power fail and low voltage alarm. When the voltage on the 12 volt power source drops below 10 volts, the zener diode D8 pushes down the base voltage of the transister Q4 causing it to turn on to sound the alarm.

The alarm battery 103 is maintained at full charge by a 4.7K dropping resistor 125 from the 12 volt supply. The alarm is shut down off by turning the main power switch off.

What is claimed is:

1. In a respiratory machine of the variable stroke, piston type having a piston reciprocable in a cylinder and a variable length connecting rod between the piston and the shaft of a motor, the improvement of
    (a) said variable length connecting rod including an elongated housing means mounted with its longitudinal axis perpendicular to the axis of the motor shaft and mounted axially and laterally off-center, thereof,
    (b) jack screw means rotatably mounted in said housing,
    (c) bar means threadedly mounted on said jack screw and arranged to be moved generally from end to end of said jack screw, (d) connecting pin means mounted on and depending from said bar interconnecting said bar means and the connecting rod,
(e) axial extending means operably connected to said jack screw means extending beyond said housing means for turning said jack screw means, and
(f) turning means inclusive of individually activated contact means positioned to contact said extending means for a short arc of each revolution of said housing means to turn said jack screw means in one direction a portion of a revolution to change the position of said bar means in said housing means.

2. In a respiratory machine according to claim 1 wherein said extending means includes a ratchet wheel for rotating said jack screw.

3. In a respiratory machine according to claim 2, wherein said turning means include a pair of spaced contacts, individually actuated to contact opposite sides of said ratchet wheel for providing rotation of said jack screw in both directions.

4. In a respiratory machine according to claim 3, wherein said spaced contacts are each actuated by a solenoid, and single switch means is arranged to operate one of said solenoids at a time.

* * * * *